United States Patent [19]

Cullen et al.

[11] 3,996,240

[45] Dec. 7, 1976

[54] HALOGENATED ALKENYL SUCCINIC ANHYDRIDE-AMINE REACTION PRODUCT

[75] Inventors: William P. Cullen, Fishkill; Harry Chafetz, Poughkeepsie, both of N.Y.

[73] Assignee: Texaco Inc., New York, N.Y.

[22] Filed: Sept. 9, 1974

[21] Appl. No.: 504,639

Related U.S. Application Data

[62] Division of Ser. No. 377,473, July 9, 1973, Pat. No. 3,864,269.

[52] U.S. Cl. ........................................ 260/326.5 F
[51] Int. Cl.$^2$ ..................................... C07D 209/32
[58] Field of Search .............. 260/326.5 F; 377/473

[56] References Cited
UNITED STATES PATENTS

| | | | |
|---|---|---|---|
| 3,219,666 | 11/1965 | Norman et al. | 260/326.5 F |
| 3,511,816 | 5/1970 | Dickakian | 260/326.5 F |

*Primary Examiner*—Dale R. Ore
*Attorney, Agent, or Firm*—T. H. Whaley; C. G. Ries; Robert A. Kulason

[57] ABSTRACT

A reaction product of detergent-dispersant properties in lubricating oil prepared by the sequential method of (1). reacting polyalkene of from 30 to 300 carbons with maleic anhydride to form alkenyl succinic anhydride, (2). contacting the alkenyl succinic anhydride with chlorine or bromine in the absence of hydroxylic and solvent compounds to form halogenated alkenyl succinic anhydride, (3). contacting the halogenated alkenyl succinic anhydride with alkylene polyamine to form crude reaction product of halogenated alkenyl succinic anhydride and alkylene polyamine and (4). preferably contacting the crude reaction product with a strong inorganic base and recovering the purified reaction product. Lubricant compositions containing a detergent-dispersant quantity of said halogenated succinic anhydride-alkylene polyamine reaction product.

8 Claims, No Drawings

HALOGENATED ALKENYL SUCCINIC ANHYDRIDE-AMINE REACTION PRODUCT

This is a division, of application Ser. No. 377,473, filed July 9, 1973, now U.S. Pat. No. 3,864,269, dated Feb. 4, 1975.

BACKGROUND OF INVENTION

An effective class of detergent-dispersants for lubricating oils taught in the prior art are the N-substituted alkenyl succinimides characterized by the formula:

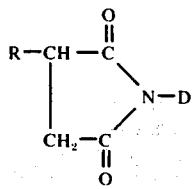

where R is alkenyl (monovalent, monoolefinic aliphatic hydrocarbon radical) of from 30 to 300 carbons and D is an amine radical selected from the group consisting of alkylene amino and polyalkylene polyamine. These prior nitrogenous dispersants are prepared by reacting polyalkene or halogenated polyalkene with maleic anhydride to form the alkenyl succinic anhydride followed by the direct reaction of the succinic anhydride with alkylene diamine or polyalkylene polyamine. The prior art succinimides, although effective detergent-dispersants are finding increasing difficulty in meeting the present day and future requirements in regard to preventing or inhibiting the formation of varnish in automotive engines.

In one effort to meet this varnish problem, the prior art, as represented by U.S. Pat. No. 3,620,977, developed a reaction product of halogenated succinyl lactone and a hydrocarbon amine by contacting alkenyl succinic anhydride with a halogen in the presence of hydroxylic compound such as water and methanol to form a halogenated succinyl lactone and then reacting this lactone with hydrocarbon amine to form a complex nitrogenous reaction product which is then subjected to a solvent extraction, e.g., methanol extraction to remove the undesired by-products. In the product defining procedure of the prior art, the hydroxylic compound is indicated to be essential.

DESCRIPTION OF THE INVENTION

We have discovered and this constitutes our invention a novel detergent-dispersant reaction product which inhibits or prevents the formation of varnish in automotive engines, lubricant compositions thereof, a method of preparation of improved economics and lubricating compositions thereof. More specifically, we have discovered a varnish inhibiting detergent-dispersant and lubricant compositions thereof which is prepared by a novel process which has the improved economics of omitting solvent and the employment of hydroxylic compounds and further has the improved feature of employing a relatively inexpensive inorganic base as a final step for product quality enhancements as opposed to the more costly liquid solvent treatments of the prior art.

Broadly, the novel detergent-dispersant is a reaction product of the halogenated alkenyl succinic anhydride and alkylene polyamine. In actuality, it is a complex mixture of many individual compounds, and therefore, is necessarily defined in terms of manufacturing method.

Hereinbefore and hereinafter the terms "halogen" and "halogenated" within the meaning of this invention are limited to chlorine and bromine.

In the first stage of the product defining procedure, alkenyl succinic anhydride of the formula:

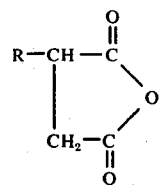

where R is a monovalent, monoolefinic polyalkene radical (alkenyl) of between about 30 and 300 carbon atoms and oil solubilizing in nature is contacted with a halogen gas selected from the group consisting of chlorine or bromine at a temperature of between about 50° and 150° C. under a pressure of between about atmospheric and 100 psig utilizing a mole ratio of anhydride to halogen of between about 1:0.5 and 1:2, the halogen introduction being normally continued until the resultant halogenated succinic anhydride has a halogen content of between about 1.5 and 5.0 wt. % usually representing a reaction time of between about 2 and 8 hours. Halogenation conditions forming essentially a monohalogenated alkenyl succinic anhydride are the most preferred. Some of the principal reactions in the first stage can be characterized by the following equations assuming chlorine and polyisobutylene succinic anhydride reactants and an unreacted polyisobutylene carry over from the anhydride preparation:

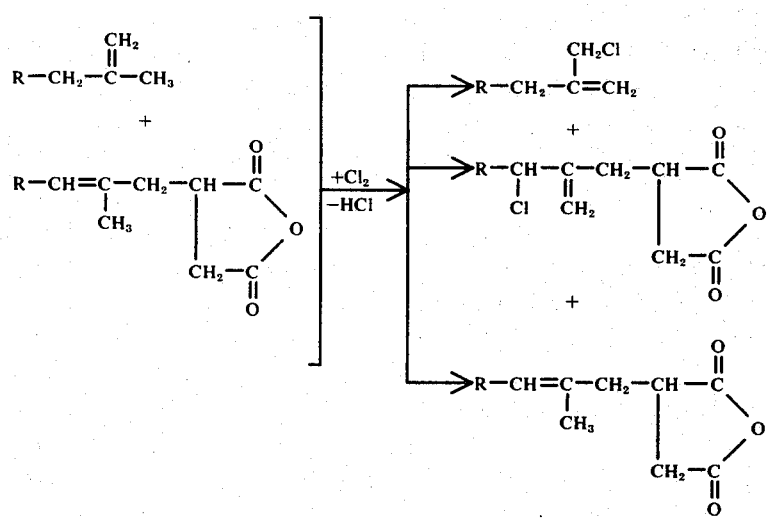

Other double bond isomers, although not shown are also present. At the close of the first stage halogenation, the halogenated intermediate mixture is preferably blown with inert gas such as nitrogen to insure essentially complete removal of volatile by-products such as hydrogen chloride. It is to be noted that one of the essential features of this stage is that it is conducted in the absence of hydroxylic solvent and under neat conditions, that is, in the absence of inert solvent.

In the second stage of the product defining procedure, the crude or purified halogenated alkenyl succinic anhydride prepared in the first stage is contacted with an alkylene polyamine characterized by the first stage halogenation is conducted in the absence of added solvent and in the absence of added hydroxylic compounds. This absence not only chracterizes the chemical nature of the final products formed but contribute to the economy of the process through the savings afforded by the non need of solvent and hydroxylic compound and the cost involved in their separation from the crude product.

Some of the principal reactions in the second stage can be characterized by the following equations wherein the reactants are ethylene diamine and crude polyisobutylene succinic anhydride.

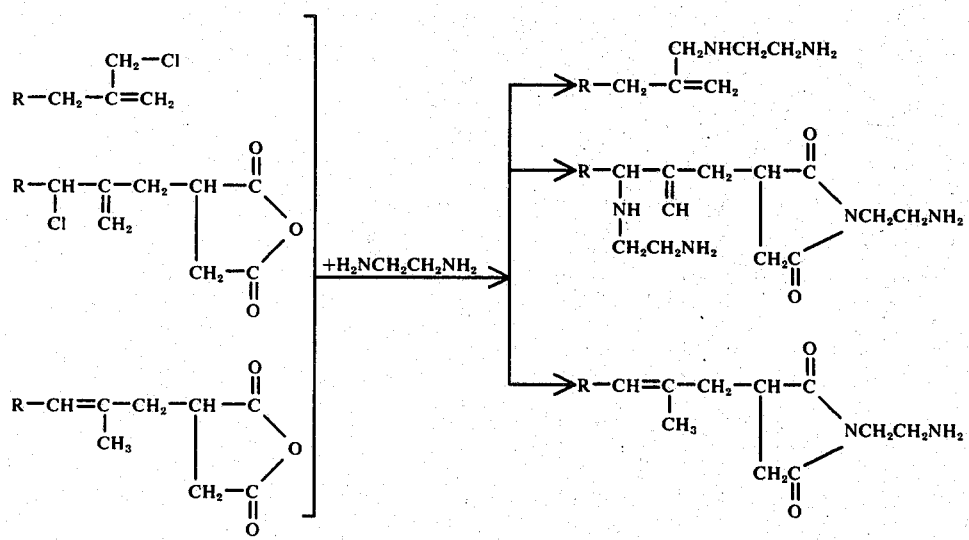

where $x$ is an integer of from 1 to 6, $y$ is an integer of from 2 to 6, and $z$ is an integer of from 0 to 4, at a temperature between about 100° and 200° C. utilizing a mole ratio of halogenated succinic anhydride intermediate to alkylene polyamine of between about 1:1 and 1:10 to form the halogenated succinic anhydride-alkylene polyamine reaction product. The amination as in In addition to the isomers shown other double bond isomers are also present.

The crude aminated reaction product can be purified by stripping off the volatile materials via inert gas blowing followed by standard filtration techniques through materials such as diatomaceous earth. However, in one embodiment of the invention the crude reaction product is diluted with an inert solvent such as liquid alkane of from 5 to 12 carbons, e.g., hexane, isooctane, whereupon an inorganic base such as alkali metal hydroxide, alkaline earth metal oxide, alkali metal carbonate and alkaline earth metal carbonate is introduced therein. The base contact with the diluted reaction product is conducted at a temperature between about 20° and 150° C. utilizing a ratio of gram atoms of halogen in the halogenated alkenyl succinic anhydride to equivalents of inorganic base of between about 1:1 and 1:2. At the end of the inorganic base treatment, the treated mixture components are separated by standard means, e.g., via filtration, followed by removal of the inert solvent, volatile amines and residual hydrogen halides via stripping with inert gas leaving the purified mixture of reaction product of halogenated alkenyl succinic anhydride and alkylene polyamine.

In respect to the alkenyl group, as heretofore stated, it represents a monovalent monoolefinic polyalkene radical of between about 30 and 300 carbons. Specific examples of alkenyl contemplated herein are polyethylene, polypropylene, polybutylene and polyisobutylene radicals and monovalent radicals of copolymers of alkenes such as copolymer of ethylene and propylene and the copolymer of propylene and butylene. Most preferably, the alkenyl group is of a molecular weight between about 900 and 2000 and a specific example of the most preferred is polyisobutylene, particularly of a molecular weight of about 1250.

Illustrative alkylene polyamine reactants contemplated herein include ethylene diamine, propylene diamine, hexamethylene diamine, diethylene triamine, and pentaethylene hexamine.

Examples of base materials for third stage utilization are sodium hydroxide, potassium hydroxide, barium oxide, calcium oxide, sodium carbonate, potassium carbonate, calcium carbonate, and barium carbonate with sodium hydroxide being the preferred material basis cost and effectiveness.

In the foregoing procedure, the absence of hydroxylic compound is critical in regard to the chemical structure of the intermediate and final products in that the presence of hydroxylic compounds of the prior art direct the reaction to form succinyl lactone materials rather than the non-lactone succinic anhydrides produced in the subject product defining method. The absence of hydroxylic compound not only produces a product of equal varnish removing ability of the prior art product, but has the added advantage of reducing the cost of additive since the cost of hydroxylic compound and necessary separation are not encountered in the subject product defining process.

A second important feature of the invention is the use of the discovery that the products could be successfully purified utilizing a relatively inexpensive inorganic base rather than the complex and costly methanol extraction which was previously believed to be necessary to maximize the effectiveness of the nitrogenous succinyl dispersant.

The lubricant compositions of the invention comprise a major amount of hydrocarbon oil of lubricating viscosity and a detergent-dispersant amount of the aforedescribed halogenated succinic anhydride-alkylene polyamine reaction product. Advantageously, in the finished lubricating oil compositions, the reaction product content ranges between about 0.1 and 10 wt. %, preferably between about 0.5 and 5 wt. %. In the lubricating oil concentrates from which the finished lubricating compositions are derived via the addition of added lubricating oil, reaction product contents between about 10 and 50 wt. % are found.

The hydrocarbon oil in the finished lubricating compositions advantageously constitutes at least about 85 wt. %, preferably between about 90 and 98 wt. %, and in the lube oil concentrates between about 50 and 90 wt. %. It is to be noted that even in the lubricating oil concentrates the reaction product exhibit detergent-dispersancy as well as varnish inhibition.

Examples of the hydrocarbon base oils contemplated herein are the naphthenic base, paraffinic base and mixed base mineral oils, lubricating oils derived from coal products and synthetic oils, e.g., alkylene polymers such as polypropylene and polyisobutylene of a molecular weight of between about 250 and 2500. Advantageously, a lubricating base oil having a lubricating oil viscosity at 100° F. of between 50 and 2000, preferably between about 100 and 600, are normally employed for the lubricant compositions and concentrates thereof. (SUS basis)

In the contemplated finished lubricating oil compositions other additives may be included in addition to the nitrogenous dispersant of the invention. These additives may be any of the suitable standard pour depressants, viscosity index improvers, oxidation and corrosion inhibitors, anti-foamants, supplementary detergent-dispersants, etc. Exactly what additional additives are included in the finished oils and the particular amounts thereof will depend on the particular use and conditions desired for the finished oil product.

Specific examples of the supplementary additives are as follows:

A widely used and suitable VI improver is the polymathacrylate having the general formula:

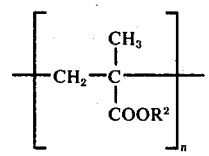

where $R^2$ is an aliphatic radical of from 1 to 20 carbons and $n$ is an integer of between about 600 and 35,000. One of the most suitable VI improvers is the tetrapolymer of butyl methacrylate, dodecyl methacrylate, octadecyl methacrylate and dimethylaminoethyl methacrylate having a respective component weight ratio in the polymer of about 4:10:5:1. The VI improvers are normally employed in the finished lubricant compositions in quantities between about 0 and 10 wt. %.

One of the commonly employed lube oil corrosion inhibitors are antioxidants of the divalent dialkyl dithiophosphates resulting from the neutralization of a $P_2S_5$-alcohol reaction product with a divalent metal or divalent metal oxide. Barium and zinc and dialkyl dithiophosphate are specific examples. Another class of antioxidants are the polyalkylated diphenylamines such as a mixture of 2,2'-diethyl-4,4'-dioctylphenylamine and 2,2'-diethyl-4-p-octyldiphenylamine. The corrosion and oxidation inhibitors are usually present in the finished lubricating oil composition in concentrations of between about 0.1 and 3 wt. %.

Examples of supplementary detergent-dispersants which can be employed are the monoethoxylated inorganic phosphorus acid free, steam hydrolyzed polyalkylene (500 – 50,000 m.w.)-$P_2S_5$ reaction product, alkaline earth metal alkylphenolates such as barium nonylphenolate, barium dodecylcresolate, calcium dodecylphenolate and the calcium carbonate overbased calcium alkaryl sulfonates formed by blowing a mixture of calcium hydroxide and calcium alkaryl sulfonate, e.g., calcium alkylbenzene sulfonate of about 900 m.w. with carbon dioxide to form a product having a total base number (TBN) of 50 or more, e.g., 300 to 400.

If antifoamants are employed in the finished compositions, one widely used class which is suitable are the dimethyl silicone polymers employed in amounts of between about 10 and 1000 ppm.

The following examples will further illustrate the product, compositions and method of the invention but are not to be construed as limitations thereof.

EXAMPLE I

This example illustrates the novel dispersant reaction products of the invention and their method of preparation.

First Stage

To a 5 liter 3-necked flask fitted with a stirrer, condenser, sodium hydroxide scrubber, glass inlet tube, thermowell and thermocouple there was charged 3600 grams (1.5 mole based on Sap. No.) of polyisobutylene (~1250 m.w.) succinic anhydride. Stirring was initiated and the polyisobutylene succinic anhydride was heated to a temperature of 125° C. wherupon chlorine gas was passed therethrough at a rate of about 500 mls. per minute for a period of about 2.5 hours and until a net weight increase of 90 grams was obtained. The product was blown with nitrogen at a temperature of about 125° C. at a rate of about 500 mls./minute for a period of about 30 minutes and until detectible evolution of hydrogen chloride and chlorine gas had ceased. The product was analyzed and determined to have a chlorine content of 2.2 wt. % containing as one principal product monochlorinated polyisobutylene (~1250 m.w.) succinic anhydride.

Second Stage

To a 12 liter 3-necked flask fitted with a stirrer, condenser, gas inlet tube, thermowell and thermocouple there were charged 4700 grams (3.4 moles) of the chlorinated succinic anhydride intermediate mixture prepared in the first stage and 600 grams (10.0 moles) of ethylene diamine. The flask was heated to reflux (~125° C.) for about 8 hours. At the end of the 8 hour period the reaction mixture was dissolved in 5 liters of heptane and the heptane solution was treated with 136 grams of powdered sodium hydroxide under conditions of agitation over a period of 0.5–2 hours. Sufficient sodium hydroxide was added to insure liberation of unreacted ethylene diamine from the ethylene diamine hydrochloride by-product. The resultant mixture was then filtered through diatomaceous earth and the heptane solution was stripped off under reduced pressure to a temperature of 100° C. affording a clear product reaction mixture which upon analysis was found to have a nitrogen content of 1.5 wt. %, a chlorine content of 0.9 wt. % and a sodium content of 155 ppm.

EXAMPLE II

This example illustrates the material difference in the hydroxylic compound free procedure of the invention and the prior art procedure employing solvent and hydroxylic compound.

The procedure of the first stage of Example I was repeated and the recovered chlorinated polyisobutylene (1250 m.w.) succinic anhydride containing reaction product was designated as Product A and set aside.

In the comparative procedure in a 2000 mls. flask as described in Example I there was charged 675 grams of polyisobutenyl (1250 m.w.) succinyl anhydride, 250 mls. of benzene and 44 mls. of methanol. The reaction mixture was heated to 50° C. and chlorine was bubbled through the reaction mixture for a period of 2 hours until a weight increase of approximately 21 grams was attained. The reaction mixture was blown with nitrogen at 50° C. for a period of 1 hour. Benzene and water were then removed at a temperature of 100° C. at a pressure of 100 mm Hg. Analysis of the resultant product was found to have a chlorine content of 2.96 wt. %. The product was designated as Product B.

Products A and B were subjected to infrared spectral analysis and Product A was found to have no change in carbonyl absorption over the non chlorinated polyisobutenyl (~1250 m.w.) succinic anhydride. However, in the case of Product B chlorinated in the presence of methanol the spectral data indicated the presence of methyl ester of an acid lactone and free carboxyl radicals also present.

EXAMPLE III

This example illustrates the lubricating oil compositions of the invention and the effectiveness of the reaction products of the invention as dispersants and varnish formation inhibitors.

The following tests were employed as measure of the dispersancy and varnish inhibiting effect of the lubricant compositions.

Bench Sludge Test (BST)

This test measures the relative dispersancy of lubricating oil compositions. In the Bench Sludge Test the oil compositions containing particular solid matter and engine blow-by agitated to evenly disperse the particulate matter throughout the oil. After centrifuge the depth of sediment is compared against a standard to show the effect of the dispersant. Sediment depths less than 1 mm indicate good dispersancy.

Bench Varnish Test (BVT)

This test is also a measure of relative dispersancy of lubricating oil compositions.

In the Bench Varnish Test a mixture containing the test oil and a diluent are heated at an elevated temperature. After heating, the turbidity of the resultant mixture is measured. A low % turbidity (0–10) are indicative of good dispersancy while high results (20–100) are indicative of oils of increasingly poor dispersancy.

Two fully formulated SAE Grade 30 lubricants were tested, namely, representative Composition C containing the chlorinated polyisobutenyl succinic anhydride-ethylene diamine reaction product of Example I and comparative control Composition D identical to Composition C except the reaction product of Example I is omitted. The Formulation C was blended so as to have a dispersant nitrogen content of 0.06 wt. %, a calcium content of 0.23 wt. % and a zinc content of 0.12 wt. %. Comparative Formulation D was also of the same blend except there was no nitrogen containing component, and therefore, no nitrogen content. Compositions of the formulations tested are as follows:

TABLE I

| Ingredients, Wt. % | C | D |
|---|---|---|
| Mineral Oil (54 SUS at 100° F.) | 92.15 | 96.15 |
| Zinc Dialkyl Dithiophosphate* | 1.20 | 1.20 |
| Overbased Calcium Alkaryl Sulfonate (900 m.w. - 300 TBN) | 1.90 | 1.90 |
| Polyalkylmethacrylate** | 0.75 | 0.75 |
| Example I Reaction Product | 4.00 | 0 |

*Alkyl is a mixture of isopropyl $C_7$ and $C_8$ alcohols
**Derived from 4:1 wt. mixture of lauryl to stearyl methacrylate monomers The above two compositions were tested in the afore-described dispersancy tests with the following results:

| Composition | BST | BVT |
|---|---|---|
| C | 0.2 | 2.5 |
| D | 1.6 | 75 |

EXAMPLE IV

This example further illustrates the lubricating oil compositions of the invention and the effectiveness of the halogenated alkenyl succinic anhydride-alkylene polyamine reaction products of the invention as dispersants and varnish inhibitors in lubricating oils.

The dispersant tests employed are described as follows:

MSCV Test

This test is the Ford Sequence VC Test and is detailed in "Multicylinder Test Sequence for Evaluating Automotive Engine Oils" ASTM Special Technical Publication under 315-E. This procedure is used to evaluate crankcase motor oils with respect to sludge and varnish deposits as well as their ability to keep the positive crankcase ventilation (PCV) valve clean and functioning properly. Ratings of 0 to 10 are given, 10 representing absolutely clean and 0 rating representing heavy sludge and varnish deposits and a clogged PCV valve.

MS II C Test

This is a light duty engine test for determination of the ability of automotive engine oil to prevent deposits forming on the PCV valve. The test operates utilizing an alternating cold and hot cycle. A 302 cubic inch engine is employed operating under the following conditions:

| | | |
|---|---|---|
| Speed, RPM | 1350 ± 10 | |
| Manifold Vacuum, in. Hg. | 17 ± 0.3 | |
| AIF ratio:1 | 14.2 ± 0.1 | |
| Cycle | 6 hrs. cold - 6 hrs. hot | |
| Temperatures, °F. | Cold Cycle | Hot Cycle |
| Jacket Out | 105 ± 2 | 190 ± 2 |
| Oil Gallery | 120 ± 2 | No cooling |
| Intake Air | 110 ± 2 | 110 ± 2 |
| Rocker covers cooling temperature | 60 ± 2 | None |

Performance of the oil is based upon the sludge deposits on the PVC valve, a rating of 10 representing clean and a rating of 0 representing heavily clogged.

L-38 Test

This test is described in detail in the Federal Test Methods Standard (FTMS) No. 791a, Method 3405. The purpose of this test is a method of determining the oxidation and copper lead bearing corrosion characteristics of crankcase oils. The performance of the test oil is judged by the weight loss of the copper lead bearing, the greater the bearing weight loss the poorer the anticorrosive ability of the crankcase oil.

Caterpillar 1-H Test

This test is described in detail in FTMS-791b-346.1. The purpose of this test is to evaluate the diesel detergent-dispersant characteristics and antiwear properties of diesel crankcase oils under high speed and medium super-charge test conditions. The engine employed is a 1Y73 single engine Caterpillar Diesel lubricant test engine. The performance of the test lubricant is judged by examination of the power section for ring sticking, piston deposits and ring, piston and liner wear. Satisfactory performance requires not more than 30 vol. % of the top groove filing (TGF) filled with deposits and not more than 50% of the second groove covered with lacquer and the piston below the second groove should be essentially clean with no ring sticking.

A fully formulated SAE Grade 30 lubricant composition was tested, namely, representative Composition E containing the nitrogenous reaction dispersant of Example I type of 1.6 wt. % nitrogen and 0.48 wt. % chlorine content. The formulation was blended to have a dispersant nitrogen content of 0.06 wt. % nitrogen, a calcium content of 0.23 wt. %, a zinc content of 0.15 wt. %. Composition of the formulation tested is as follows:

TABLE III

| Ingredients, Weight % | E |
|---|---|
| Mineral Oil (54 SUS at 100° F.) | 92.20 |
| Zinc Dialkyl Dithiophosphate* | 1.40 |
| Overbased Calcium Alkaryl Sulfonate (900 m.w. - 300+ TBN) | 1.90 |
| Polyalkylmethacrylate** | 0.75 |
| Dispersant of Ex. I type | 3.75 |

*Alkyl is derived from a mixture of isopropyl, $C_7$ and $C_8$ alcohols.
**Derived from a terpolymer of butyl methacrylate, lauryl methacrylate, stearyl methacrylate and dimethylaminoethyl methacrylate in approximate weight ratio of 21/50/25/4 as about a 40 wt. % solution in mineral oil.

The above composition was tested in the aforedescribed dispersancy test with the following results:

TABLE III

| Test | Rating E |
|---|---|
| MSVC | |
| Sludge | 9.7 |
| Varnish | 8.5 |
| PSV | 9.3 |
| MS II C | 8.7 |
| L-38 | |
| B.W.L. (Mg.) | 34 |
| Cat 1-H (480 Hrs) | |
| T.G.F., % vol. | 0 |
| 1st Land, % covered | 28 |
| 2nd Groove, % cov. | 3 |
| Below 2nd Groove | Clean |

As can be seen from the foregoing, the complex nitrogenous dispersant is a very effective dispersant for both moderate temperature gasoline engine and high temperature diesel engine operation.

We claim:
1. A method of preparing a halogenated alkenyl succinic anhydride-alkylene polyamine reaction product comprising reacting in the absence of hydroxylic and solvent compounds an alkenyl succinic anhydride characterized by the formula:

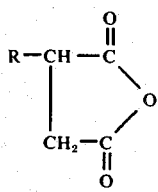

where R is a monoolefinic, monovalent polyalkene radical of from 30 to 300 carbons with a halogen selected from the group consisting of chlorine and bromine at a temperature between about 50° and 150° C. utilizing a mole ratio of alkenyl succinic anhydride to said halogen of between about 1:0.5 and 1:2 to form a monohaloalkenyl succinic anhydride containing intermediate, contacting in the absence of hydroxylic and solvent compounds said intermediate with an alkylene polyamine of the formula:

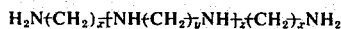

where $x$ is an integer of from 1 to 6, $y$ is an integer from 2 to 6 and $z$ is an integer from 0 to 4 at a temperature between about 100° and 200° C. utilizing a mole ratio of said intermediate to alkylene polyamine of between about 1:1 and 1:10 to form said halogenated alkenyl succinic anhydride-alkylene polyamine reaction product.

2. A method of preparing a base treated halogenated alkenyl succinic anhydride-alkylene polyamine reaction product comprising reacting in the absence of hydroxylic and solvent compounds an alkenyl succinic anhydride characterized by the formula:

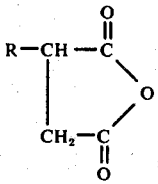

where R is a monoolefinic, monovalent polyalkene radical of from 30 to 300 carbons with a halogen selected from the group consisting of chlorine and bromine at a temperature between about 50° and 150° C. utilizing a mole ratio of alkenyl succinic anhydride to halogen of between about 1:0.5 and 1:2 to form a halogenated alkenyl succinic anhydride containing intermediate, contacting in the absence of hydroxylic and solvent compounds said intermediate with an alkylene polyamine of the formula:

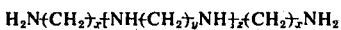

where $x$ is an integer from 1 to 6, $y$ is an integer from 2 to 6 and $z$ is an integer from 0 to 4 at a temperature between about 100° and 200° C. utilizing a mole ratio of said intermediate to alkylene polyamine of between about 1:1 and 1:10 to form said halogenated alkenyl succinic anhydride-alkylene polyamine reaction product, and contacting said product with an inorganic base selected from the group consisting of alkali metal hydroxide, alkaline earth metal oxide, alkali metal carbonate and alkaline earth metal carbonate at a temperature between about 20° and 150° C. utilizing a ratio of gram atoms of halogen in said halogenated alkenyl succinic anhydride to equivalents of said base of between about 1:1 and 1:2 and recovering said base treated halogenated alkenyl succinic anhydride reaction product from the base treated mixture.

3. A method in accordance with claim 1 wherein said R is polyisobutylene, said halogen is chlorine and said alkylene polyamine is ethylene diamine.

4. A method in accordance with claim 2 wherein said R is polyisobutylene, said halogen is chlorine, said alkylene polyamine is ethylene diamine, and said base is sodium hydroxide.

5. A complex reaction product of halogenated alkenyl succinic anhydride and alkylene polyamine of detergent-dispersant properties in lubricating oil prepared by the method comprising reacting in the absence of hydrolic and solvent compounds an alkenyl succinic anhydride characterized by the formula:

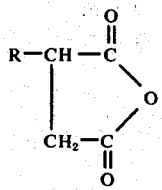

where R is a monoolefinic, monovalent polyalkene radical of from 30 to 300 carbons with a halogen selected from the group consisting of chlorine and bromine at a temperature between about 50° and 150° C. utilizing a mole ratio of alkenyl succinic anhydride to said halogen of between about 1:0.5 and 1:2 to form a haloalkenyl succinic anhydride containing intermediate, contacting in the absence of hydroxylic and solvent compounds said intermediate with an alkylene polyamine of the formula:

where $x$ is an integer of from 1 to 6, $y$ is an integer from 2 to 6 and $z$ is an integer from 0 to 4 at a temperature between about 100° and 200° C. utilizing a mole ratio of said intermediate to alkylene polyamine of between about 1:1 and 1:10 to form said halogenated alkenyl succinic anhydride-alkylene polyamine reaction product.

6. A complex base treated reaction product of halogenated alkenyl succinic anhydride and alkylene polyamine of detergent-dispersant properties in lubricating oil prepared by the method comprising reacting in the absence of hydroxylic and solvent compounds an alkenyl succinic anhydride characterized by the formula:

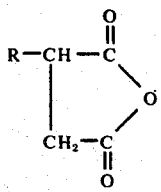

where R is a monoolefinic, monovalent polyalkene radical of from 30 to 300 carbons with a halogen selected from the group consisting of chlorine and bromine at a temperature between about 50° and 150° C. utilizing a mole ratio of alkenyl succinic anhydride to said halogen of between about 1:0.5 and 1:2 to form a haloalkenyl succinic anhydride containing intermediate, contacting in the absence of hydroxylic and solvent compounds said intermediate with an alkylene polyamine of the formula:

where $x$ is an integer from 1 to 6, $y$ is an integer from 2 to 6 and $z$ is an integer from 0 to 4 at a temperature between about 100° and 200° C. utilizing a mole ratio of said intermediate to alkylene polyamine of between about 1:1 and 1:10 to form said halogenated alkenyl succinic anhydride-alkylene polyamine reaction product, and contacting said product with a base selected from the group consisting of alkali metal hydroxide, alkaline earth metal oxide, alkali metal carbonate, and alkaline earth metal carbonate at a temperature between about 20° and 150° C. utilizing a ratio of gram atoms of halogen in said halogenated alkenyl succinic anhydride to equivalents of said base of between about 1:1 and 1:2 and recovering said base treated halogenated alkenyl succinic anhydride reaction product from the base treated mixture.

7. A complex reaction product of claim 5 wherein said R is polyisobutylene, said halogen is chlorine, and said alkylene polyamine is ethylene diamine.

8. A complex base treated reaction product of claim 6 wherein said R is polyisobutylene, said halogen is chlorine, said alkylene polyamine is ethylene diamine and said base is sodium hydroxide.

* * * * *